US00PP27819P2

(12) United States Plant Patent
Dummen

(10) Patent No.: US PP27,819 P2
(45) Date of Patent: Mar. 28, 2017

(54) ***PELARGONIUM* PLANT NAMED 'DUEBEZREIMP'**

(50) Latin Name: *Pelargonium zonale*
Varietal Denomination: Duebezreimp

(71) Applicant: Tobias Dummen, Rheinberg (DE)

(72) Inventor: Tobias Dummen, Rheinberg (DE)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 14/757,052

(22) Filed: Nov. 11, 2015

(51) Int. Cl.
*A01H 5/02* (2006.01)

(52) U.S. Cl.
USPC ..... Plt./330

(58) Field of Classification Search
USPC ..... Plt./330
CPC ..... A01H 5/0277
See application file for complete search history.

*Primary Examiner* — Kent L Bell
(74) *Attorney, Agent, or Firm* — C. A. Whealy

(57) ABSTRACT

A new and distinct cultivar of Zonal Geranium plant named 'Duebezreimp', characterized by its broadly upright plant habit; moderately vigorous growth habit; freely basal branching habit; dark green-colored and zoned leaves; freely flowering habit; large intense red-colored flowers; and good garden performance.

1 Drawing Sheet

Botanical designation: *Pelargonium zonale.*
Cultivar denomination: 'DUEBEZREIMP'.

BACKGROUND OF THE INVENTION

The present invention relates to a new and distinct cultivar of Zonal Geranium plant, botanically known as *Pelargonium zonale*, and hereinafter referred to by the name 'Duebezreimp'.

The new Zonal Geranium plant is a product of a planned breeding program conducted by the Inventor in Koka, Oromia, Ethiopia and Rheinberg, Germany. The objective of the breeding program is to create new vigorous Zonal Geranium plants with dark-colored leaves and numerous large attractive flowers.

The new Zonal Geranium plant originated from a cross-pollination made by the Inventor in 2011 in Koka, Oromia, Ethiopia of a proprietary selection of *Pelargonium zonale* identified as code number 60022, not patented, as the female, or seed, parent with a proprietary selection of *Pelargonium zonale* identified as code number 88862, not patented, as the male, or pollen, parent. The new Zonal Geranium plant was discovered and selected by the Inventor as a single flowering plant from within the progeny of the stated cross-pollination in a controlled greenhouse environment in Rheinberg, Germany during the summer of 2012.

Asexual reproduction of the new Zonal Geranium plant by vegetative terminal cuttings since October, 2012, in a controlled greenhouse environment in Rheinberg, Germany has shown that the unique features of this new Zonal Geranium plant are stable and reproduced true to type in successive generations.

SUMMARY OF THE INVENTION

Plants of the new Zonal Geranium have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Duebezreimp'. These characteristics in combination distinguish 'Duebezreimp' as a new and distinct Zonal Geranium plant:

1. Broadly upright plant habit.
2. Moderately vigorous growth habit.
3. Freely basal branching habit.
4. Dark green-colored and zoned leaves.
5. Freely flowering habit.
6. Large intense red-colored flowers.
7. Good garden performance.

Plants of the new Zonal Geranium differ primarily from plants of the female parent selection in plant habit as plants of the female parent are more trailing than and not as upright as plants of the new Zonal Geranium.

Plants of the new Zonal Geranium differ primarily from plants of the male parent selection in flower color as plants of the male parent selection have pink-colored flowers.

Plants of the new Zonal Geranium can be compared to plants of the *Pelargonium zonale* 'Duecumbadar', disclosed in U.S. Plant Pat. No. 23,808. In side-by-side comparisons conducted in Rheinberg, Germany, plants of the new Zonal Geranium differed primarily from plants of 'Duecumbadar' in the following characteristics:

1. Plants of the new Zonal Geranium were not as freely branching than plants of 'Duecumbadar'.
2. Plants of the new Zonal Geranium and 'Duecumbadar' differed in flower color as plants of 'Duecumbadar' had less intense red-colored flowers.

BRIEF DESCRIPTION OF THE PHOTOGRAPH

The accompanying colored photograph illustrates the overall appearance of the new Zonal Geranium plant showing the colors as true as it is reasonably possible to obtain in colored reproductions of this type. Colors in the photograph may differ slightly from the color values cited in the detailed botanical description which accurately describe the colors of the new Zonal Geranium plant.

The photograph comprises a side perspective view of a typical flowering plant of 'Duebezreimp' grown in a container.

DETAILED BOTANICAL DESCRIPTION

The aforementioned photograph and following observations and measurements describe plants grown during the summer in 10.5-cm containers in a glass-covered greenhouse in Rheinberg, Germany and under cultural practices typical of commercial *Pelargonium* production. During the production of the plants, day and night temperatures averaged 18° C. and light levels averaged 4,500 lux. Plants were pinched one time three weeks after planting and were 13 weeks old when the photograph and the description were taken. In the detailed description, color references are made to The Royal Horticultural Society Colour Chart, 2007 Edition, except where general terms of ordinary dictionary significance are used.

Botanical classification: *Pelargonium zonale* 'Duebezreimp'.

Parentage:

*Female, or seed, parent*.—Proprietary selection of *Pelargonium zonale* identified as code number 60022, not patented.

*Male or pollen parent*.—Proprietary selection of *Pelargonium zonale* identified as code number 88862, not patented.

Propagation:

*Type*.—By vegetative terminal cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Broadly upright plant habit; uniformly rounded; densely foliated; moderately vigorous growth habit.

*Branching habit*.—Freely basal branching habit with about eleven basal branches developing per plant.

*Plant height to top of flower umbels*.—About 38 cm.

*Plant height to top of foliar plane*.—About 33 cm.

*Plant width*.—About 65 cm.

*Lateral branches*.—Length: About 25 cm. Diameter: About 1 cm. Internode length: About 1.9 cm. Texture: Pubescent. Strength: Moderately strong. Color: Close to 145B.

Leaf description:

*Arrangement*.—Alternate; simple.

*Length*.—About 6.3 cm.

*Width*.—About 10 cm.

*Shape*.—Roughly reniform.

*Apex*.—Acute.

*Base*.—Cordate.

*Margin*.—Crenate.

*Venation pattern*.—Palmate.

*Texture, upper surface*.—Pubescent.

*Texture, lower surface*.—Smooth, glabrous.

*Luster, upper and lower surfaces*.—Matte.

*Color*.—Developing and fully expanded leaves, upper surface: Close to 137B; venation, close to 137B. Developing and fully expanded leaves, lower surface: Close to 147B; venation, close to 144B.

*Zonation pattern*.—Width: About 1.6 cm. Distance from leaf margin: About 1 cm. Color: Darker than 137B.

*Petioles*.—Length: About 8 cm. Diameter: About 2 mm. Texture, upper and lower surfaces: Smooth, glabrous. Color, upper and lower surfaces: Close to 144B.

Flower description:

*Flower arrangement*.—Single type flowers arranged in rounded hemispherical umbels arising from apical leaf axils; umbels displayed above the foliar plane on moderately strong peduncles; flowers face mostly upright to outwardly depending on position in the umbel.

*Fragrance*.—None detected.

*Flowering habit*.—Freely flowering habit, about 33 flowers developing per umbel and numerous flower umbels developing per plant; at one time, about 275 flowers and flower buds per plant.

*Flowering season*.—Year-round under greenhouse conditions; in outdoor nurseries and gardens in Germany, flowering is continuous from spring throughout the summer until the autumn; plants begin to flower about eight weeks after planting.

*Flower longevity*.—Individual flowers last about five to seven days on the plant; flowers persistent.

*Umbel height*.—About 6 cm.

*Umbel diameter*.—About 8.5 cm.

*Flower diameter*.—About 4 cm by 4.5 cm.

*Flower depth (height)*.—About 3 cm.

*Flower buds*.—Length: About 1.9 cm. Diameter: About 9 mm. Shape: Ovoid. Color: Close to 45A.

*Petals*.—Quantity per flower: About five arranged in a single whorl. Length: About 3 cm. Width: About 2.1 cm. Shape: Obovate. Apex: Rounded. Base: Attenuate. Margin: Sinuate. Texture, upper and lower surfaces: Smooth, glabrous. Luster, upper and lower surfaces: Matte. Color: When opening and fully opened, upper surface: Close to 45B; color does not fade with development. When opening and fully opened, lower surface: Close to 45D; color does not fade with development.

*Petaloids*.—None observed on plants of the new Zonal Geranium.

*Sepals*.—Quantity per flower: Five arranged in a single whorl. Length: About 1 cm. Width: About 3 mm. Shape: Ensiform. Apex: Apiculate. Margin: Entire. Texture, upper and lower surfaces: Smooth, glabrous. Luster, upper and lower surfaces: Matte. Color, upper and lower surfaces: Close to 144B tinged with close to 179B.

*Peduncles* (*umbel stems*).—Length: About 15.8 cm. Diameter: About 5 mm. Strength: Moderately strong. Aspect: Mostly upright. Texture: Smooth, glabrous. Color: Close to 144B.

*Pedicels* (*individual flower stems*).—Length: About 3.1 cm. Diameter: About 1 mm. Strength: Moderately strong. Texture: Smooth, glabrous. Color: Close to 144B tinged with close to 179B.

*Reproductive organs*.—Androecium: Stamen quantity per flower: About eight. Filament length: About 5.8 mm. Filament color: Close to 60B. Anther length: About 2 mm. Anther shape: Oblong. Anther color: Close to 60A. Pollen amount: Moderate. Pollen color: Close to 28A. Gynoecium: Pistil quantity per flower: One. Pistil length: About 8.4 mm. Stigma shape: Tapering. Stigma color: Close to 60B. Style length: About 2 mm. Style color: Close to 60B. Ovary color: Close to 144B.

*Seeds and fruits*.—Seed and fruit development have not been observed on plants of the new Zonal Geranium.

Disease & pest resistance: Plants of the new Zonal Geranium have not been observed to be resistant to pathogens and pests common to Zonal Geranium plants.

Garden performance: Plants of the new Zonal Geranium have been observed have good garden performance and to tolerate rain, wind, and temperatures ranging from about 5° C. to about 40° C.

It is claimed:

1. A new and distinct Zonal Geranium plant named 'Duebezreimp' as illustrated and described.

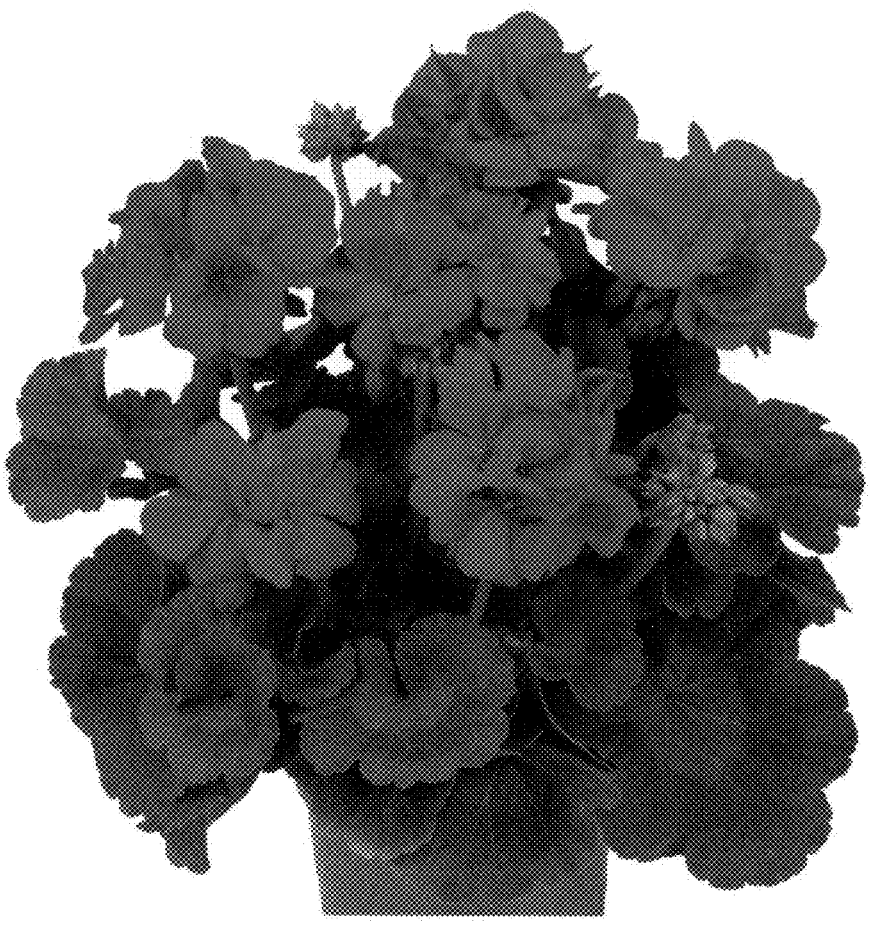

* * * * *